US010894095B2

(12) United States Patent
Sohn et al.

(10) Patent No.: US 10,894,095 B2
(45) Date of Patent: Jan. 19, 2021

(54) MULTIPURPOSE MEDICAL IMAGE INDICATOR AND METHOD FOR MANUFACTURING THE SAME

(71) Applicant: National Cancer Center, Goyang-si (KR)

(72) Inventors: Dae Kyung Sohn, Seoul (KR); Yong Doo Choi, Anyang-si (KR); Kwang Gi Kim, Seoul (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 16/721,215

(22) Filed: Dec. 19, 2019

(65) Prior Publication Data

US 2020/0171175 A1 Jun. 4, 2020

Related U.S. Application Data

(62) Division of application No. 15/302,732, filed as application No. PCT/KR2015/003489 on Apr. 7, 2015, now Pat. No. 10,548,992.

(30) Foreign Application Priority Data

Apr. 11, 2014 (KR) .................. 10-2014-0043485

(51) Int. Cl.
| A61B 5/055 | (2006.01) |
| A61K 49/12 | (2006.01) |
| A61K 49/00 | (2006.01) |
| A61B 5/00 | (2006.01) |
| A61K 49/04 | (2006.01) |
| A61K 49/06 | (2006.01) |
| A61B 6/03 | (2006.01) |
| A61B 6/00 | (2006.01) |
| A61B 6/12 | (2006.01) |
| A61B 1/04 | (2006.01) |
| G01R 33/56 | (2006.01) |

(52) U.S. Cl.
CPC .............. *A61K 49/12* (2013.01); *A61B 5/055* (2013.01); *A61B 5/684* (2013.01); *A61K 49/0021* (2013.01); *A61K 49/0034* (2013.01); *A61K 49/04* (2013.01); *A61B 1/043* (2013.01); *A61B 5/0071* (2013.01); *A61B 6/03* (2013.01); *A61B 6/12* (2013.01); *A61B 6/481* (2013.01); *A61K 49/06* (2013.01); *G01R 33/5601* (2013.01)

(58) Field of Classification Search
None
See application file for complete search history.

(56) References Cited

U.S. PATENT DOCUMENTS

| 3,026,587 A | 3/1962 | Spencer |
| 6,689,297 B1 | 2/2004 | Mizuta et al. |
| 2003/0198674 A1 | 10/2003 | Curatolo et al. |
| 2006/0138381 A1 | 6/2006 | Shibata et al. |
| 2008/0181965 A1 | 8/2008 | Leon et al. |
| 2009/0133605 A1 | 5/2009 | Butler et al. |
| 2009/0280064 A1 | 11/2009 | Papineni et al. |
| 2011/0022161 A1 | 1/2011 | Uhrich et al. |

FOREIGN PATENT DOCUMENTS

| EP | 0808175 B1 | 7/2002 |
| EP | 1582539 A1 | 10/2005 |
| JP | 09-056721 A | 3/1997 |
| JP | 10-055911 A | 2/1998 |
| JP | 10-513175 A | 12/1998 |
| JP | 11-514986 A | 12/1999 |
| JP | 2005-507393 A | 3/2005 |
| JP | 2005-522424 A | 7/2005 |
| JP | 2009-516036 A | 4/2009 |
| JP | 2009-539501 A | 11/2009 |
| JP | 2012-501355 A | 1/2012 |
| JP | 4963789 B2 | 6/2012 |
| KR | 10-2012-0015849 A | 2/2012 |
| WO | 97/10811 A1 | 3/1997 |
| WO | 03/28700 A2 | 4/2003 |
| WO | 20041056894 A1 | 7/2004 |

OTHER PUBLICATIONS

Aprem et al. (J. Elastomers Plastics 2003, 35, 29-55).*
Supplementary European Search Report and Written Opinion received for EP Patent Application No. 15777505.7, dated Oct. 11, 2017, 6 pages.

(Continued)

*Primary Examiner* — Michael G. Hartley
*Assistant Examiner* — Melissa J Perreira
(74) *Attorney, Agent, or Firm* — Womble Bond Dickinson (US) LLP

(57) ABSTRACT

The present disclosure concerns a medical image indicator. More particularly, it concerns the multipurpose medical image indicator including more than one of fluorophores and MRI contrast agent/CT contrast agent and method for manufacturing same. Responding to a demand for non-invasive and effective way of marking lesions, the present disclosure provides a method for manufacturing the multipurpose medical image indicator including a provision of rubber material fluid composition; a mixing of the rubber material fluid composition and fluorophores; and a transfiguring and drying of the mixture and the multipurpose medical image indicator manufactured according to the method. Further, the present disclosure provides a ligation device for endoscope including the multipurpose medical image indicator.

4 Claims, 5 Drawing Sheets

(56) References Cited

OTHER PUBLICATIONS

Office Action received for Korean Patent Application No. 10-2014-0043485, dated Oct. 16, 2015, 3 pages of Original Document Only.
Office Action received for Japanese Patent Application No. 2016-561269, dated Mar. 6, 2018, 3 pages of Original Document Only.
Office Action received for Japanese Patent Application No. 2016-561269, dated Dec. 4, 2018, 4 pages of Original Document Only.
Office Action received for European Patent Application No. 15777505.7, dated Mar. 22, 2019, 4 pages.
Office Action received for European Patent Application No. 15777505.7, dated Jul. 17, 2018, 5 pages.
Office Action received for Chinese Patent Application No. 201580019226.9, dated Oct. 31, 2018, 13 pages (7 pages of English Translation and 6 pages of Office Action).
International Search Report and Written Opinion received for PCT Patent Application No. PCT/KR2015/003489, dated Jul. 9, 2015, 14 pages (7 pages of English Translation and 7 pages of Original Document).
International Preliminary Report on Patentability received for PCT Patent Application No. PCT/KR2015/003489, dated Oct. 20, 2016, 12 pages (7 pages of English Translation and 5 pages of Original Document).
Yanase et al., J. Appl. Polym. Sci., 1993, 50, 765-776.

* cited by examiner

MULTIPURPOSE MEDICAL IMAGE INDICATOR AND METHOD FOR MANUFACTURING THE SAME

TECHNICAL FIELD

The present disclosure relates to medical image indicator, and more particularly, to multipurpose medical imagining indicator which include more than one fluorophores and MRI contrast agent or CT contrast agent and method for manufacturing same.

Further, the present disclosure relates to a ligation device for endoscope including multipurpose medical imagining indicator.

BACKGROUND

Laparoscopic surgery has been widely applied to cure malignant disease as well as benign disease. Laparoscopic surgery is considered to be the basis of surgical operations as robot operations using laparoscopic surgery has been introduced.

The advantages of laparoscopic surgery compared to abdominal section are pain reduction, early recovery of patients, and reduction of hospitalization period. And the problem of laparoscopic surgery compared to abdominal section that has been pointed out so far is that it is impossible to check tumor sites and organs by directly sensing them with hands.

Particularly, in case of early gastric cancer or colon cancer, it is important to mark the location of tumor before the surgery since it is difficult to directly observe lesions at laparoscopic surgery. Further, in case of early colon cancer, although the methods for locating lesion including barium enema, tattoo method under colonoscopy, clip installation around lesion, and observation of colonoscopy during operation are currently used, the problem of usefulness and side effects has been raised as these methods are not suitable for laparoscopic surgery.

Accordingly, there has been a demand for a new non-invasive method of locating lesion that allows real-time visual identification of a state of installation at marked lesion before or during operation and a site that needs to be removed during operation.

SUMMARY OF INVENTION

Solution to Problem

The present disclosure is directed to providing the multipurpose medical image indicator that precisely identify marked site using a non-invasive method.

The present disclosure is also directed to providing the multipurpose medical imagining indicator including MRI contrast agent or CT contrast agent.

The present disclosure is also directed to providing a ligation device for endoscope including the multipurpose medical image indicator.

Technical Solution

The present disclosure provides the multipurpose medical image indicator including rubber material and fluorophores.

More particularly, the rubber material is one of rubber, latex-free rubber, NFR, Neoprene, natural latex, and synthesis latex. Further, the fluorophores according to an exemplary embodiment of the present disclosure provides the multipurpose medical image indicator including more than one of Indocyanine Green, Rose Bengal, dye affiliated with ATTO, dye affiliated with Alexa, Rhodamine, Fluorescein, Cumarin, Naphthalimide, Benzoxanthen and Acridine.

Desirably, the multipurpose medical image indicator further include an MRI contrast agent or a CT agent.

More desirably, the MRI contrast agent is composed of a gadolinium complex, a mangan complex or an oxidized steel nanoparticle, the CT agent is composed of a metal, a complex including iodine, or a nanoparticle.

The present disclosure is also directed to providing a method for manufacturing multipurpose medical image indicator including a provision of rubber material fluid composition; a mixing of the rubber material fluid composition and fluorophores; and transfiguring and drying of the mixture.

To be more particular, the mixing of the rubber material is a method for manufacturing multipurpose medical image indicator including a rubber material, a crosslinking agent, an accelerator, an active agent, and an anti-aging agent. To be more particular, the crosslinking agent is a sulfur crosslinking agent; the accelerator is an accelerator that includes more than one of sulfide, sulfenamide, and carbamate; the active agent is an active agent including more than one of zinc oxide or stearate; and the anti-aging agent is the anti-aging agent including more than one of amines, imidazole, and quinone.

Desirably, a method for manufacturing multipurpose medical imagining indicator may include sulfur cross linker 1.0 to 2.0 weight, carbamate activator 0.5 to 1.0 weight, zinc oxide 0.5 to 1.0 weight, and anti-aging agent 0.8 to 1.6 weight per rubber material 100 weight of the mixing of the rubber material.

The present disclosure provides the multipurpose medical imagining indicator including rubber material and fluorescent; and a ligation device for endoscope including a ligation assembly.

Effects of Invention

The multipurpose medical image indicator according to the exemplary embodiment of the present disclosure are capable of accurately and swiftly detecting the lesion side by marking before the laparoscope operation.

Further, a method for manufacturing the multipurpose medical imagining indicator is capable of reducing the operation time and minimizing the range of normal tissues to be surgically removed by accurately detecting the marked part with a noninvasive method.

Furthermore, the present disclosure provides a band ligation device for endoscope including more than one of the medical image indicator which includes fluorescent and MRI contrast agent or CT contrast agent, accurately display the location of a tumor by a noninvasive method, and are thus useful for imaging inspection before and after operation and radiotherapy.

METHOD FOR CARRYING OUT THE INVENTION

Figure 1:
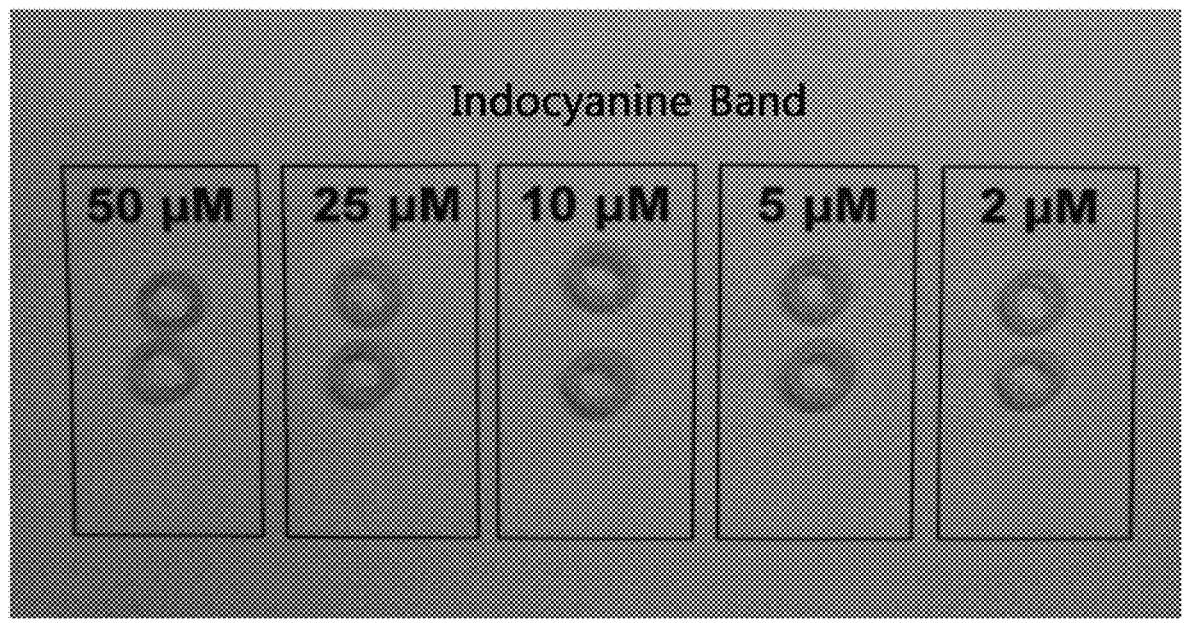
FIG. 1 is a drawing illustrating a fluorescence rubber band including Indocyanine green according to an exemplary embodiment of the present disclosure.

The present invention will be described more fully hereinafter with exemplary embodiments of the invention. As those skilled in the art would realize, the described embodiments may be modified in various different ways, all without departing from the spirit or scope of the present disclosure.

The present disclosure provides multipurpose medical image indicator including rubber material and fluorophores. And more particularly, it provides the multipurpose medical image indicator wherein the rubber material is one of rubber, latex-free rubber, NFR, Neoprene, natural latex, and synthesis latex thereof.

The 'latex' is a secreting fluid of natural rubber collected from the Para rubber tree, rubber particles are dispersed and floated using water as dispersion medium on colloid. The natural latex collected from the rubber tree is used as a base material for various industrial rubber applied products. The SBR latex (Styrene-Butadiene Rubber latex) is an artificial latex made by dispersing soft particles of rubber or resin in the water, the main ingredient is SBR thereof. The rubber without latex (NFR) is a natural milk-like substance discovered in plants. Neoprene is synthetic rubber variously used in different industries. It is one of the rubber materials with excellent chemical resistance and weatherability.

The fluorophores according to an exemplary embodiment of the present disclosure includes more than one of Indocyanine Green, Rose Bengal, dye affiliated with ATTO, dye affiliated with Alexa, Rhodamine, Fluorescein, Cumarin, Naphthalimide, Benzoxanthen and Acridine.

Indocyanine green (IGC) is a near infrared ray fluorescence material (Absorption Wavelength 600 nm-900 nm), and a relatively safe reagent which is also used for the angiography. Rose Bengal is a fluorescence material used for nuclear medicine scan of liver and includes Iodine which has contrast effects in X-ray. ATTO type dye and Alexa type dye are also near infrared ray dyes (Absorption Wavelength 650 nm~900 nm) and show improved permeability compared to that of other fluorescence materials with the wavelength below 650 nm. Rhodamine (Absorption Wavelength 530 nm to 580 nm) is a generic term for Rhodamine B, one of the basic dyes, and its derivatives. It is blue fluorescence color or yellowish red.

When the above fluorescence materials are used for the medical image indicator, it is possible to reduce operation time by accurately detecting the marked areas by non-invasive method and to gain the effects of minimizing the range of normal tissues.

The present disclosure is directed to providing the multipurpose medical image indicator including rubber material, fluorophores, and an MRI contrast agent. When the MRI contrast agent is injected into the human body, it takes the role of widening the gaps of relaxation rates between tissues by changing the relaxation rates of tissues and the role of emphasizing the contrast between the tissues by changing MRI signals. For GMRI contrast material, ionized gadolinium (Gd)(III) complex and neutral gadolinium (Gd)(III) complex are used. More particularly, for the MRI contrast agent, gadolinium complexes, manganese complexes, and iron oxide nano capsule are used. More particularly, TM(Feridex), an iron oxide nano capsule contrast agent, and TM(Onmiscan), a gadolinium complex, were used for the MRI contrast agent in an exemplary embodiment of the present disclosure, but the materials used for the present disclosure are not necessarily limited to the materials.

Further, the present disclosure is directed to providing the multipurpose medical image indicator further including a CT contrast agent in addition to the rubber material and fluorophores. The CT contrast agent is a material used for emphasizing the shadow in case of an X-ray shooting. A metal, a compound including iodine, or a compound including nano particles was used for an exemplary embodiment of the present disclosure, but the materials used for the present disclosure are not limited to them.

The present disclosure is further directed to providing the multipurpose imaging indicator including a provision of rubber material fluid composition; a mixing of the rubber material fluid composition and fluorophores; and transfiguring and drying of the mixture.

More particularly, the mixing of the rubber material includes a rubber material, a crosslinking agent, an accelerator, and active agent, an anti-aging agent. To be more particular, the present disclosure provides a method for manufacturing multipurpose medical image indicator wherein the crosslinking agent is a sulfur crosslinking agent; the accelerator is an accelerator including more than one of sulfide, sulfonamide, and carbamate; the active agent is an active agent including more than one of zinc oxide or stearate; and the anti-aging agent is the anti-aging agent including more than one of amines, imidazole, and quinone.

According to an exemplary embodiment of the present disclosure, the sulfur-cross linker functions as a linker between the polymeric chains of the rubber material. It is possible to use conventional vulcanizates with abundant sulfur content, and it is also possible to receive the effects of improving thermal resistance and crosslink density by reducing gaps between rubber molecule chains with the use of the semi efficient vulcanizates which promotes sulfur linking.

The accelerator takes the role of improving durability by promoting the crosslink response of the sulfur, and sulfide type accelerators, sulfonamide type accelerators and carbamate type accelerators are used. Particularly, the accelerator used for an exemplary embodiment of the present disclosure may be an accelerator including one of the sulfide type accelerators, sulfonamide type accelerators and carbamate type accelerators. More particularly, the carbamate type accelerators used for an exemplary embodiment of the present disclosure are either diethyl dithiocarbamate or dibuthyl dithiocarbamate, but the materials used for the present disclosure are not necessarily limited to the materials.

The active agent used for an exemplary embodiment of the present disclosure takes the role of activating the crosslinking agent. More particularly, it is the active agent which includes more than one of zinc oxide (ZnO) and stearic acid.

To be more particular, the active agent according to an exemplary embodiment of the present disclosure is zinc oxide (ZnO).

Further, the anti-aging agent is a material added to prevent the oxidization of rubber. The anti-aging agent used for an exemplary embodiment of the present disclosure includes more than one of amines, imidazole, and quinone to improve heat resistance and fatigue resistance, but the materials used for the present disclosure are not necessarily limited to the materials.

Desirably, in the mixing of the rubber material, sulfur cross linker is 1.0 to 2.0 weight, carbamate activator is 0.5 to 1.0 weight, zinc oxide is 0.5 to 1.0 weight, and amines type anti-aging agent is 0.8 to 1.6 weight per rubber material 100 weight of the mixing of the rubber material.

When the sulfur cross linker is below 1.0 weight per rubber material 100 weight, durability degrades. When it exceeds 2.0 weight, durability also degrades.

When the carbamate activator is below 0.5 weight per rubber material 100 weight, linking by vulcanization is impossible due to the absence of the effectual crosslinking system. And when it exceeds 1.0 weight, the problem may happen in the process due to the generation of Scorch.

When the zinc oxide is below 0.5 weight per rubber material 100 weight, the speed of sulfur crosslinking reaction decreases. When it exceeds 1.0 weight, the problem may happen in terms of productivity as the reaction speed increases.

When the amines type anti-aging agent is below 0.8 weight per rubber material 100 weight, it is impossible to expect anti-aging effects. When it exceeds 1.6 weight, the price competitiveness may decreases.

More desirably, in the mixing of the rubber material, the sulfur cross linker is 1.5 weight, the carbamate activator is 0.8 weight, the zinc oxide is 0.8 weight, and the amines type anti-aging agent is 1.2 weight per rubber material 100 weight.

An exemplary embodiment of the present disclosure provides the method for manufacturing the multipurpose medical image indicator including more than one of the fluorophores among Indocyanine Green, Rose Bengal, ATTO type dye, Alexa type dye, Rhodamine, Fluorescein, Cumarin, Naphthalimide, Benzoxanthen and Acridine.

In the drying step of the method for manufacturing the multipurpose medical image indicator, drying is desirably performed in 70° C. to 100° C. It is to help crosslinking reaction that the drying step is needed in the exemplary embodiment of the present disclosure. In the exemplary embodiment of the present disclosure, the multipurpose medical image indicator manufactured through the transfiguration was dried in 100° C. for one hour, but the example is not intended to be limiting the invention. More desirably, depending on the fluorophores, it is possible to maintain the stability of fluorophores by performing drying and crosslinking reaction for longer hours in the room temperature or low temperature below 60° C.

Exemplary Embodiment 1

Preparation of the Mixing of Rubber Material

We prepared a latex fluid composition by mixing sulfur cross linker 1.5 weight, diethyl dithiocarbamate accelerator 0.8 weight, zinc oxide 0.8 weight, and amines anti-aging agent 1.2 weight per natural rubber (latex) and natural rubber 100 weight into solution.

Manufacturing of Fluorescence Rubber Band

Manufacturing Example 1

We melted Indocyanine green (purchased at Sigma-Aldrich, molecular weight 774.9 g/mol) 1.345 mg into 100 μL dimethylsulfoxide) solvent.

We took 58 μL from the Indocyanine green solution and added it into 20 mL latex solution. And we completely mixed the Indocyanine green solution, fluorophores, with the latex solution by vortexing.

Through the manufacturing method, we gained mixed liquor wherein the concentration of the Indocyanine green in the latex solution is 50 μM.

We could acquire a rubber band by coating the above mixed liquor to the surface of Pasteur pipette, by drying it in the room temperature for five minutes, and by removing the coated rubber from the above pipette.

Then, we performed drying and crosslinking reaction of the fluorescent rubber band including the Indocyanine green in the oven of 100° C. for one hour.

Manufacturing Example 2

We manufactured the fluorescent rubber band using the same method used in the Manufacturing Example 1 except the condition that the concentration of the Indocyanine green in the latex solution is 25 μM.

Manufacturing Example 3

We manufactured the fluorescent rubber band using the same method used in the Manufacturing Example 1 except the condition that the concentration of the Indocyanine green in the latex solution is 10 μM.

Manufacturing Example 4

We manufactured the fluorescent rubber band using the same method used in the Manufacturing Example 1 except the condition that the concentration of the Indocyanine green in the latex solution is 5 μM.

Manufacturing Example 5

We manufactured the fluorescent rubber band using the same method used in the Manufacturing Example 1 except the condition that the concentration of the Indocyanine green in the latex solution is 2 μM.

The shape and color of the fluorescent rubber band manufactured by the Manufacturing Examples 1 to 5 are illustrated in FIG. 1. Although the shape of the fluorescent rubber band is illustrated as a circular link type in FIG. 1, the materials used for the present disclosure are not necessarily limited to the materials.

Evaluation 1. Fluorescence Signal Characteristic Evaluation

TABLE 1

|  | Manufacturing Example 1 | Manufacturing Example 2 | Manufacturing Example 3 | Manufacturing Example 4 | Manufacturing Example 5 |
| --- | --- | --- | --- | --- | --- |
| Indocyanine green(ICG) concentration | 50 μM | 25 Mm | 10 Mm | 5 μM | 2 μM |

The [Table 1] shows the concentration of the Indocyanine green of each fluorescent rubber band manufactured in the Example 1.

Figure 2:
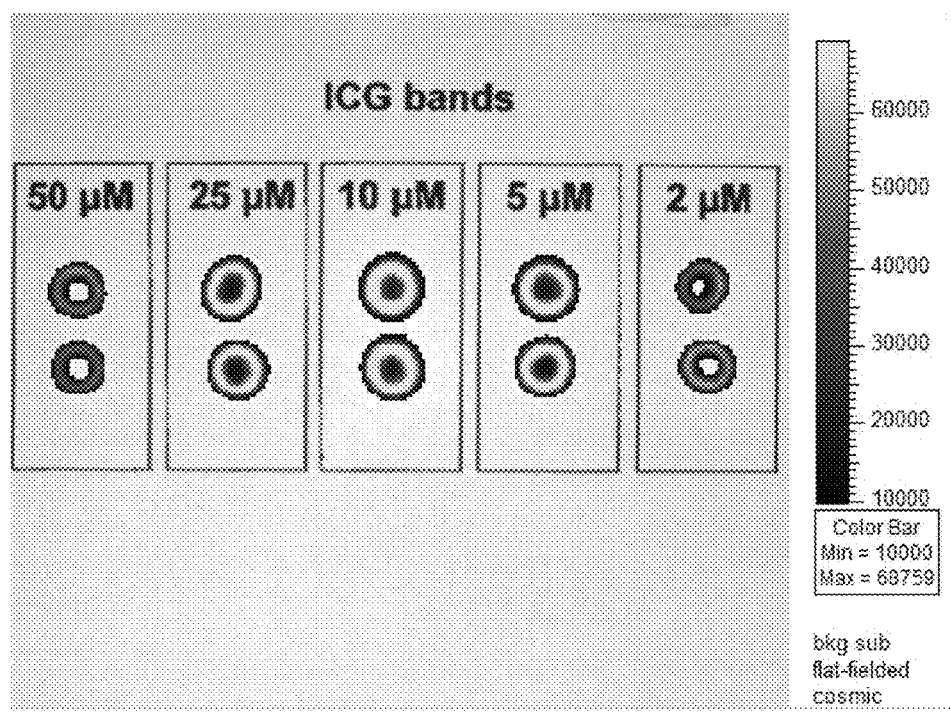
FIG. 2 is a drawing mixing a white image and a fluorescence image of a fluorescence rubber band according to an exemplary embodiment of the present disclosure.

To evaluate the fluorescent characteristic of the fluorescent rubber bands manufactured above, we acquired the white light images and fluorescent images of each fluorescent rubber band in Manufacturing Examples 1 to 5 by using the fluorescent visual devices (IVIS Lumina XR, Xenogen Corporation-Caliper, Calif., USA). FIG. 2 shows them.

More particularly, FIG. 2 is a fusion image of the white light images and fluorescent images of each fluorescent rubber band manufactured according to the manufacturing methods of the Examples 1 to 5, and the fluorescent signal was the most intense in the fluorescent rubber band of Manufacturing Example 5 with the lowest concentration of the Indocyanine green.

The intensity of the fluorescent signal gradually increased when the Indocyanine green concentration was up to 10 μM (Manufacturing Examples 3 to 5). However, the intensity of the fluorescent signal rather decreased when the Indocyanine green concentration was higher than this. The intensity of the fluorescent signal of Manufacturing Example 1 was the lowest when the Indocyanine green concentration was highest.

Manufacturing Example 6

We prepared ATTO647N dye (purchased at ATTO-TEC GmbH company) which emits fluorescence in the 600 nm wavelength.

To manufacture latex mixed liquor wherein the concentration of the ATTO647N is 50 μM, we melted 0.746 mg of the ATTO647N into solution 20 mL. Except the process, we manufactured a fluorescent rubber band using the same method as used in the Manufacturing Example 1.

Manufacturing Example 7

We prepared Rhodamine 6G dye (purchased at Sigma-Aldrich) which emits fluorescence in the 500 nm wavelength.

To manufacture latex mixed liquor wherein the concentration of the Rhodamine 6G is 50 μM, we melted 0.48 mg of the Rhodamine 6G into solution 20 mL. Except the process, we manufactured a fluorescent rubber band using the same method as used in the Manufacturing Example 1.

Figure 3:
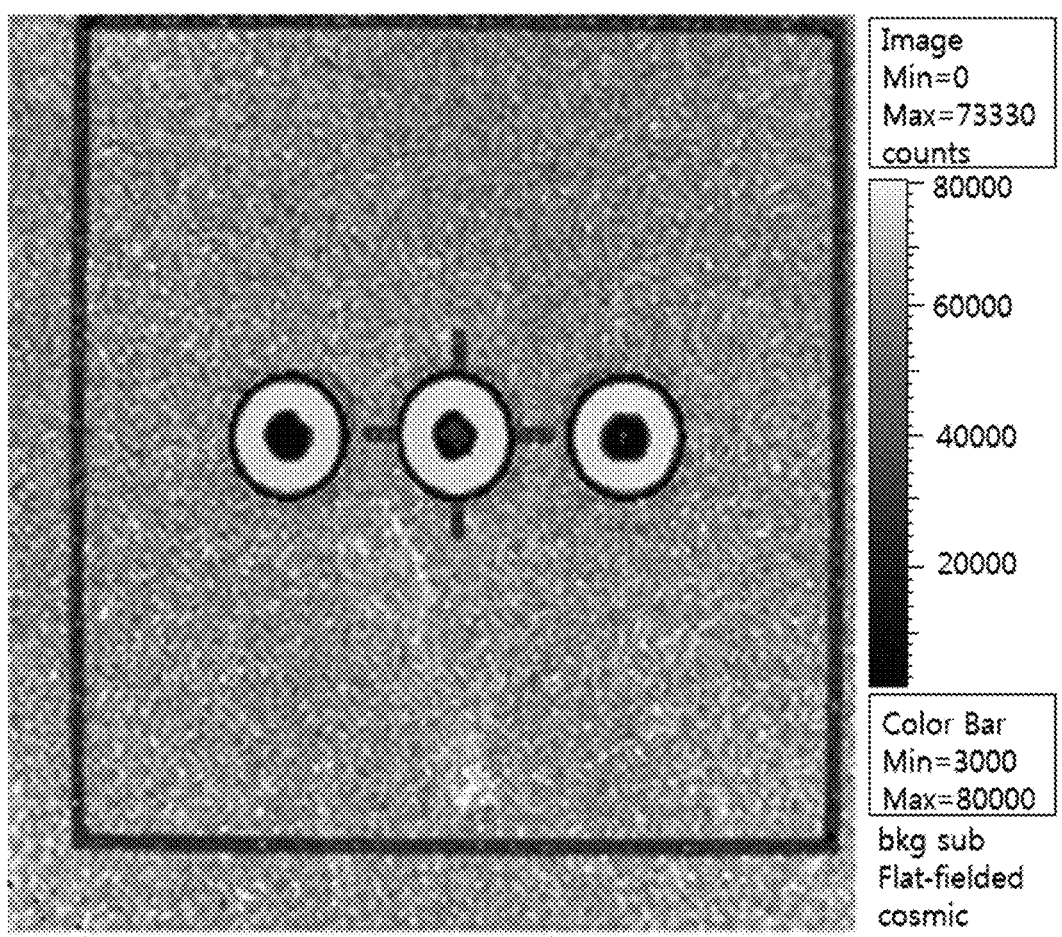
FIG. 3 is a drawing mixing white light and fluorescence image of a fluorescence rubber band including ATTO647N according to an exemplary embodiment of the present disclosure.
Figure 4:
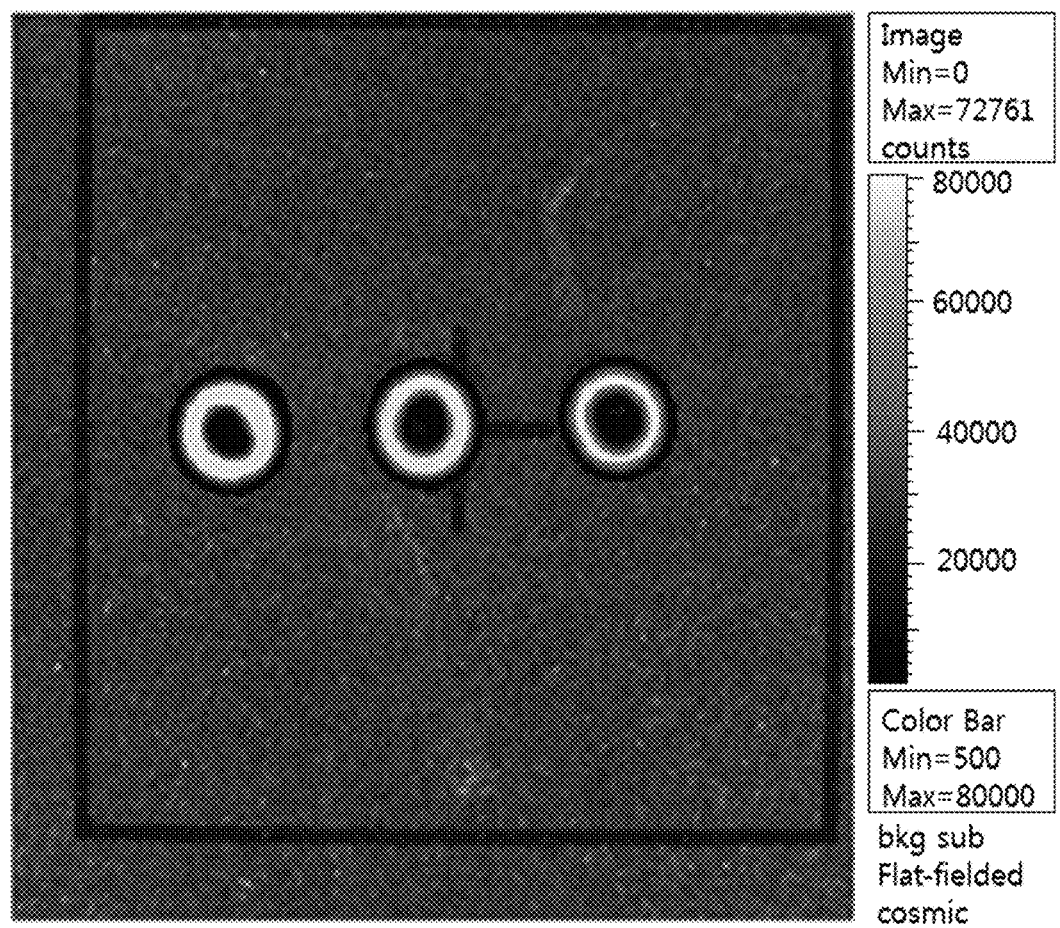
FIG. 4 is a drawing mixing white light and fluorescence image of a fluorescence rubber band including Rhodamine 6G according to an exemplary embodiment of the present disclosure.
Figure 5:
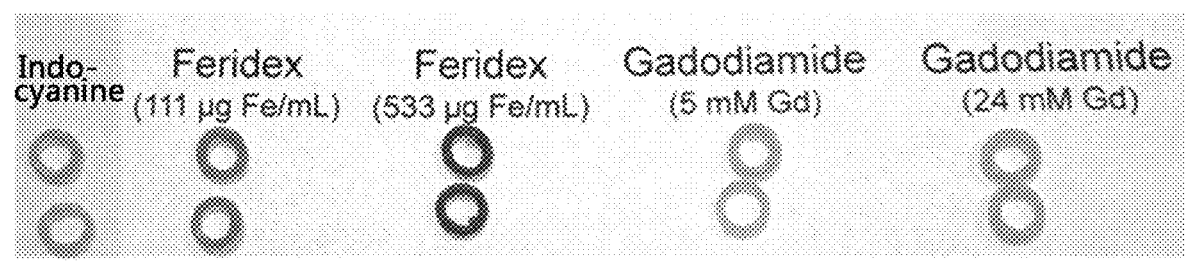
FIG. 5 is a drawing illustrating a fluorescence rubber band including MRI contrast agents, Feridex and Gadodiamide, according to an exemplary embodiment of the present disclosure.
Figure 6:
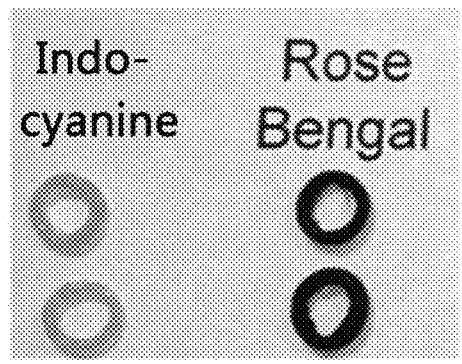
FIG. 6 is a drawing illustrating a fluorescence rubber band including Rose Bengal, a CT contrast agent according to an exemplary embodiment of the present disclosure.

The fluorescent characteristics of the fluorescent rubber bands manufactured according to the manufacturing methods in Manufacturing Examples 6 and 7 are illustrated in FIG. 3 and FIG. 4. All the fluorescent rubber bands manufactured according to the manufacturing methods in Manufacturing Examples 6 and 7 emit intense fluorescent signals.

By installing more than one of the fluorescent rubber bands manufactured according to an exemplary embodiment of the present disclosure on a ligation device for endoscope, it is possible to use them for marking lesions and treatment of them.

Furthermore, the present disclosure provides the multi-purpose medical image indicator further including the mixing of MRI contrast agent after the mixing of the fluorescent dye into the rubber material and before the transfiguring and drying of the mixture. More particularly, the MRI contrast agent is one of the gadolinium complexes, manganese complexes, and complexes including iron oxide nano capsules.

Exemplary Embodiment 2

Preparation of Latex Solution Mixed with Fluorescent Dye

We prepared latex solution according to the manufacturing method of the [Exemplary Embodiment 1].

And, we melted 0.67 mg of the Indocyanine green into 50 μL of dimethylsulfoxide solvent.

We took 17 μL from the Indocyanine green liquor and added it to 30 mL of latex solution. And we melted it by vortexing and let the Indocyanine green liquor and the latex solution entirely mixed.

According to the manufacturing method, we acquired a mixture wherein the concentration of the Indocyanine green in the latex solution is 10 μM.

Manufacturing of the Rubber Band Capable of MRI Images

We directly used I.V. Feridex (purchased at Taejoon Pharmaceutical Company, 1.2 μg Fe/mL), MRI contrast agent, and OMISCAN, Gadodiamide, (500 mM, purchased at GE Healthcare) as these industrial products are dispersed in the solution.

Manufacturing Example 8

We added 50 μL of Feridex I.V., MRI contrast agent, into 5 Ml of the latex solution mixed with the Indocyanine green with the 10 μM concentration and performed vortexing.

According to the above manufacturing method, we prepared a solution in which Feridex is melted with 111 μg Fe/mL concentration of fluid composition.

Manufacturing Example 9

We prepared the solution in which Feridex is melted with 533 μg Fe/mL concentration of fluid composition in the same method as used in the Manufacturing Example 8, except that we used the 250 μL of Feridex I.V. for MRI contrast agent.

Manufacturing Example 10

We prepared the solution in which Gadodiamide is melted with 5 mM Gd concentration in the same method as used in the Manufacturing Example 8, except that we used the 50 μL of OMISCAN, Gadodiamide, for MRI contrast agent.

Manufacturing Example 11

We prepared the solution in which Gadodiamide is melted with 24 mM Gd concentration in the same method as used in the Manufacturing Example 8, except that we used the 250 μL of OMISCAN, Gadodiamide, for MRI contrast agent.

We acquired a rubber band by coating the mixture according to the Manufacturing Example 8 to 11 on the surface of the pasteur pipette, drying it in the room temperature for 5 minutes, and taking off the coated rubber from the pipette.

Then, we proceeded drying and crosslinking reaction of the fluorescent rubber band including the contrast agent in the 100° C. oven for one hour.

Further, the present disclosure provides the method for manufacturing the multipurpose medical image indicator further including the mixing of CT contrast agent after the mixing of the fluorescent dye into the rubber material and before transfiguring and drying of the mixture. More particularly, the CT contrast agent may be one of the compound including metal or iodine or the compound composed of nano particles. More particularly, in the exemplary embodiment of the present disclosure, Rose Bengal is used, but the example is not intended to be limiting the invention. Rose Bengal includes iodine which has contrast effects for X-ray, is in solid state, and soluble.

Exemplary Embodiment 3

Preparation of Latex Aqueous Solution Mixed with Fluorophores

We prepared the latex solution according to the manufacturing method of [Exemplary Embodiment 1].

Then, we melted 0.67 mg of the Indocyanine green into the 50 μL of dimethylsulfoxide solvent.

We took 17 μL of the Indocyanine green into the 30 mL of latex solution, and entirely mixed the Indocyanine green and the latex solution by melting them through vortexing.

According to the manufacturing method above, we acquired a mixture wherein the concentration of the Indocyanine green in the latex solution is 10 μM.

Manufacturing of a Rubber Band Capable of CT (computed tomography) Image

Manufacturing Example 12

We prepared Rose Bengal, a reagent including iodine, for CT contrast agent.

We added 121.5 mg of Rose Bengal into the 5 mL of latex solution mixed with the Indocyanine green of 10 μM concentration and performed vortexing.

According to the above manufacturing method, we prepared a solution mixed with melted iodine of 100 mM concentration.

We acquired a rubber band by coating the liquor on the surface of the pasteur pipette, drying it in the room temperature for 5 minutes, and taking off the coated rubber from the pipette.

Then, we proceeded drying and crosslinking reaction of the fluorescent rubber band including the CT contrast agent in the 100° C. oven for one hour.

Evaluation 2. CT Image Evaluation

Figure 7:
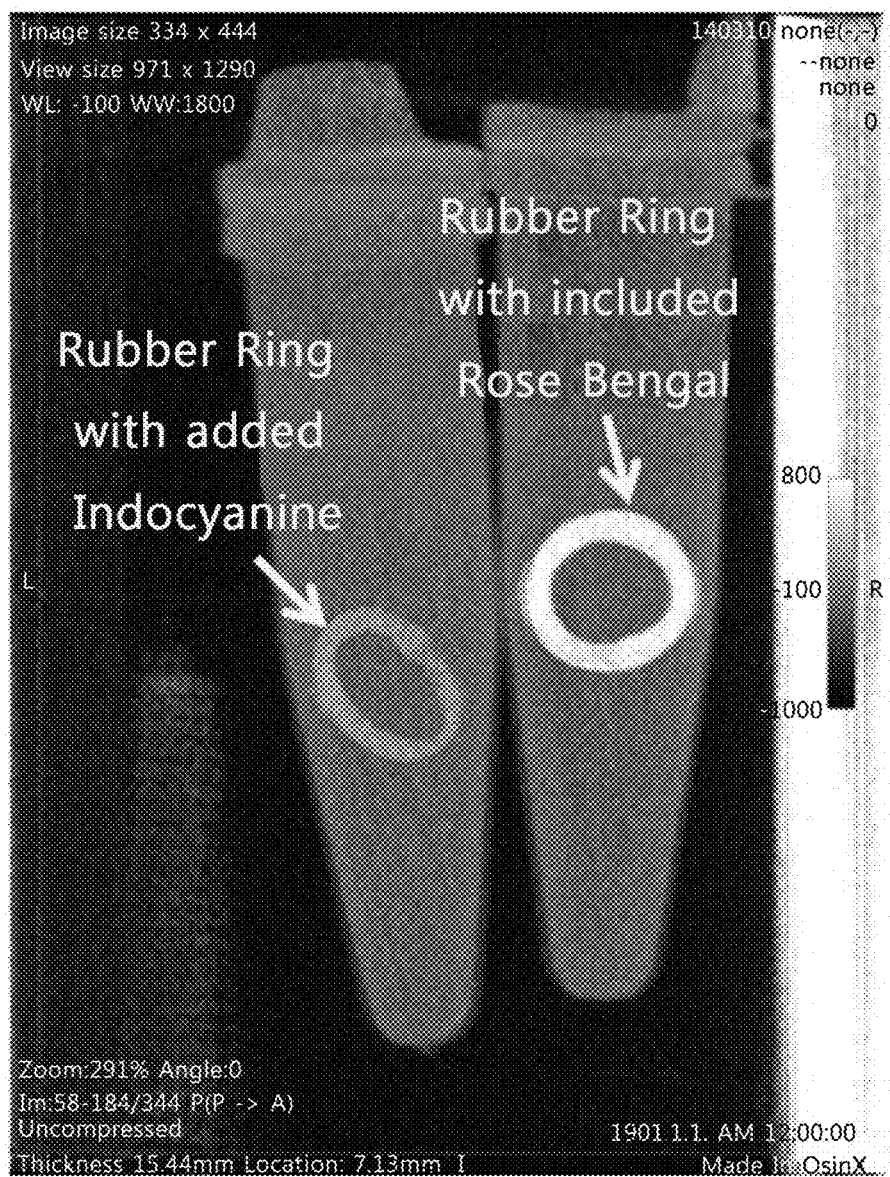
FIG. 7 is a CT image photo of a fluorescence rubber band including Rose Bengal, a CT contrast agent.
Figure 8:
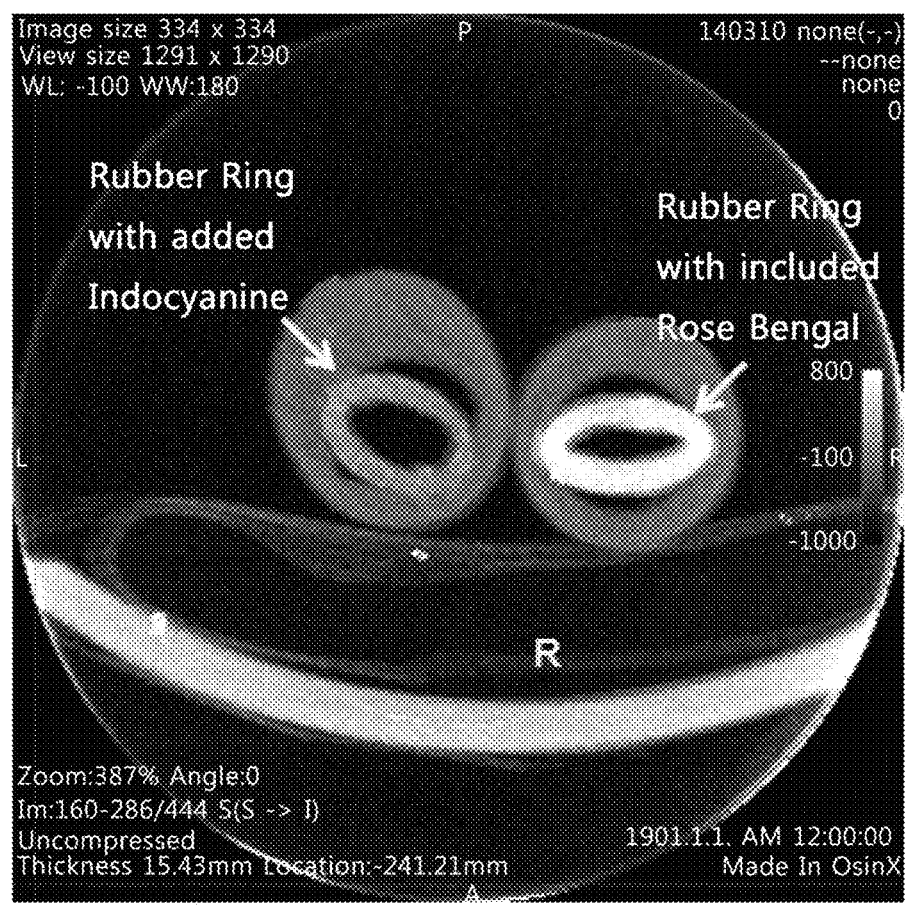
FIG. 8 is a CT image photo of a fluorescence rubber band including Rose Bengal, a CT contrast agent.

FIGS. 7 and 8 show CT image photos of the Manufacturing Example 1 and Manufacturing Example 12. More particularly, they are images taken by putting the fluorescent rubber bands manufactured in the Manufacturing Example 1 and 12 into plastic tubes.

The fluorescent rubber band further including Rose Bengal in the Manufacturing Example 12 shows more intensive CT contrast effect compared to the fluorescent rubber band only including Indocyanine green, a fluorescent dye, in the Manufacturing Example 1.

Further, the present disclosure provides the multipurpose medical imagining indicator including rubber material and fluorophores manufactured by the above method and a litigation device for endoscope including a ligation assembly. Particularly, the litigation device for endoscope includes more than one of the multipurpose medical imagining indicator manufactured by the above exemplary embodiment 1 to 3. Furthermore, the multipurpose medical imagining indicator manufactured by an exemplary embodiment of the present disclosure is capable of being easily applied to the various conventional band ligation device.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Accordingly, the scope of the present disclosure shall be determined only according to the attached claims.

What is claimed is:

1. A method for manufacturing multipurpose medical image indicator, comprising,
    providing a rubber material fluid composition that includes an anti-aging agent which includes more than one of amines, imidazole, and quinone;
    mixing of the rubber material fluid composition and fluorophores; and
    transfiguring and drying of the mixture to form a fluorescent rubber band.

2. The method for manufacturing multipurpose medical image indicator of claim 1,
    wherein the rubber material fluid composition further includes an additional rubber material, a crosslinking agent, an accelerator, and an active agent.

3. The method for manufacturing multipurpose medical image indicator of claim 2,
    wherein in the rubber material fluid composition,
    the crosslinking agent is a sulfur crosslinking agent;
    the accelerator includes more than one of sulfide, sulfenamide, and carbamate; and
    the active agent includes more than one of zinc oxide or stearate.

4. The method for manufacturing multipurpose medical image indicator of claim 3,
    wherein 100 weight of the rubber material fluid composition comprises,
    sulfur cross linker 1.0 to 2.0 weight, carbamate activator 0.5 to 1.0 weight, zinc oxide 0.5 to 1.0 weight, and anti-aging agent 0.8 to 1.6 weight.

* * * * *